US00PP24051P3

(12) United States Plant Patent
Jauchen

(10) Patent No.: US PP24,051 P3
(45) Date of Patent: Dec. 3, 2013

(54) MINIATURE ROSE PLANT 'PACNINETYEIGHT'

(50) Latin Name: *Rosa hybrida*
Varietal Denomination: PACninetyeight

(76) Inventor: Daniel Jauchen, Santa Barbara, CA (US)

( * ) Notice: Subject to any disclaimer, the term of this patent is extended or adjusted under 35 U.S.C. 154(b) by 101 days.

(21) Appl. No.: 13/317,583

(22) Filed: Oct. 24, 2011

(65) Prior Publication Data

US 2013/0104266 P1 Apr. 25, 2013

(51) Int. Cl.
*A01H 5/00* (2006.01)

(52) U.S. Cl.
USPC ..... Plt./117

(58) Field of Classification Search
USPC ..... Plt./117
See application file for complete search history.

*Primary Examiner* — June Hwu

(57) ABSTRACT

A new miniature rose plant which has abundant, white colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Botanical designation: *Rosa hybrida.*
Variety denomination: 'PACninetyeight'.

BACKGROUND OF THE INVENTION

The present invention constitutes a new and distinct variety of miniature rose plant, which was developed by artificially pollinating an unnamed seedling (not patented) with an unnamed seedling (not patented). The two parents were crossed in the summer of 2001 and the resulting seed was sown in December 2001, in a controlled glasshouse environment. Out of these seedlings one seedling was selected, as the new variety and named 'PACninetyeight'. The new rose may be distinguished from its seed parent, an unnamed seedling, by the following combination of characteristics:

1. 'PACninetyeight' has small double flowers, while the unnamed seedling has medium double flowers.
2. 'PACninetyeight' has white colored petals, while the unnamed seedling has off white petals.

The new variety may distinguish from its pollen parent, an unnamed seedling, by the following combination of characteristics:

1. 'PACninetyeight', has small double flowers, while the unnamed seedling has medium double flowers.
2. 'PACninetyeight' has white colored petals, while the unnamed seedling has off white petals.

BRIEF SUMMARY OF THE INVENTION

Initial asexual reproduction of 'PACninetyeight' by cuttings was first done in Santa Barbara, Calif., USA. This initial and other subsequent propagation conducted in controlled environments have demonstrated that the characteristics of 'PACninetyeight' are true to type and are transmitted one generation to the next. 'PACninetyeight' is a low and compact miniature rose with good vigor. The objective of the hybridization of this rose variety for commercial greenhouse culture was to create a new and distinct variety with:

1. Uniform and abundant flowers with good keeping ability;
2. Attractive long lasting foliage and compact growth;
3. Year round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type, known to the inventor, and distinguish 'PACninetyeight' from all other varieties of which I am aware.

The seeds from hybridization were planted in a controlled environment and evaluations were conducted on the resulting plants. 'PACninetyeight' was selected by, Daniel Jauchen, in his development program in Santa Barbara, Calif., USA.

BRIEF DESCRIPTIONS OF THE DRAWINGS

The accompanying color illustrations show as true as is reasonably to obtain in color photographs of this type, the typical characteristics of the buds, flowers, leaves, stems of 'PACninetyeight'. Specifically illustrated in the drawings:

1: Young shoot.
2: Bud before opening the sepals.
3: Bud at the stage of opening the sepals.
4: Bud at the stage of opening the petals.
5: Flower during course of opening.
6: Open flower—plan view—obverse.
7: Open flower—plan view—reverse.
8: Fully open flower—plan view—obverse.
9: Fully open flower—plan view—reverse.
10: Receptacle showing stamens and pistils.
11: Receptacle showing pistils (stamens and sepals removed).
12: Flower petals, detached—inner surface.
13: Flower petals, detached—outer surface.
14: Bare stem exhibiting thorns and flower attachment.
15: Three leaflets upper side.
16: Three leaflets reverse side.

17: Five leaflets upper side.
18: Five leaflets reverse side.

DETAILED BOTANICAL DESCRIPTION OF THE VARIETY

The following is a detailed description of the Miniature Rose: Rosa hybrida 'PACninetyeight'.

The following observations, measurements, values and comparisons describe plants grown in glass houses in Santa Barbara, Calif., USA.

The age of the observed plants were 3 months after propagation by cuttings, and produced as flowering pot plants in container of 10 centimeter in diameter. Environmental conditions in the cultivation area for the observed plants, has been temperatures from 64 to 78 degree Fahrenheit, and 10 to 20 hours day length with assimilation light. Light levels from 600 foot candle to 6000 foot candle. The relative humidity has been ranging from 50 to 85%.

Color references are made using The Royal Horticultural Society (London, England) Colour Chart, 1995, except where common terms of color are used. For a comparison, the nearest existing rose variety is 'JENeight', a rose variety described and illustrated in U.S. Plant Pat. No. 18,179.

Chart 1 details several physical characteristics of 'PACninetyeight' and 'JENeight'.

CHART 1

| | 'PACninetyeight' | 'JENeight' |
|---|---|---|
| Petal color, Upper surface | White Group 155A | White Group 155D |
| Petal color, Reverse surface | White Group 155A | White Group 155D |
| Petal count | 35 to 40 | 25-30 |

Parents: Unnamed seedling times unnamed seedling.

Classification:

*Botanical.*—*Rosa hybrida.*

*Commercial.*—Miniature.

Plant:

*Plant growth.*—Moderately vigorous. Grows compact upright to bushy. When grown as 10 cm pot plant, the average height of the plant itself is 18 cm to 20 cm, and average width is 20 cm. When grown as a 15 cm pot plant, the average height of the plant itself is 22 cm to 27 cm, and average width is 30 cm.

Stem:

*Color.*—Young wood: Yellow-Green Group 144C. Older wood: Green Group 139B.

*Thorns.*—Incidence: 1 to 2 per stem. Size: 1 to 2 mm. Form: Deep concave. Color: Greyed-Red Group 181B.

*Surface.*—Young wood: Smooth. Older wood: Smooth.

*Stem diameter.*—Width: 1 mm to 2 mm. Length: 177 mm to 190 mm.

*Internode length.*—15 mm to 20 mm.

*Numbers of internodes.*—4 to 5.

Plant foliage: Leaves arranged alternately, compound with 3 to 5 leaflets per leaf, generally symmetrical, abundant, and flat in aspect. Stipules at petiole base.

*Quantity of leaves.*—5 to 6 per lateral branch.

*Leaf size.*—Length 35 mm to 55 mm, width 30 mm to 45 mm.

*Petioles.*—Color: Green Group 137C. Margins: Entire. Length: 10 mm to 15 mm Diameter: about 0.5 mm to 1 mm.

*Stipules.*—Size: Length 2 mm to 5 mm, width 1 mm to 2 mm. Surface upper and lower: Smooth. Color for upper surface: Green Group 141A. Color for lower surface: Green Group 138A. Margins: Entire. Apex shape: Spinose.

*Rachis.*—Color: Green Group 137C. Margins: Entire. Length: 5 mm to 10 mm. Diameter: 0.5 mm to 1 mm.

*Pedicel.*—Color: Green Group 143C. Texture: Pubescent. Size: Length: 10 mm to 20 mm. Width: 3 mm to 4 mm.

*Leaflets.*—Edge: Serrated. Serration: Single. Shape: Ovate with acute apex and obtuse base. Upper and lower texture: Smooth. Appearance: Dull. Size: length: 10 mm to 25 mm, width: 10 mm to 15 mm. Color: Young foliage: Upper surface: Green Group 137C. Edge with intonations of Greyed-Red 180A. Lower surface: Green Group 138B. Color: Mature foliage: Upper surface: Between Green Group 139A-B. Lower surface: Green Group 139B. Leaf vein color: Upper surface: Green Group 143A. Reverse surface: Green Group 144C.

Inflorescence:

*Blooming habit.*—Recurrent.

*Number of flowers.*—Generally one to three buds per flowering stem.

*Average size.*—Width: 11 mm. Length: 25 mm.

*Peduncle.*—Color: Green Group 144B. Upper and lower texture: Smooth. Length: 15 mm to 30 mm Diameter: 1.5 mm to 2 mm. Strength: Upright.

*Receptacle.*—Surface: Smooth, glabrous. Shape: Funnel-shaped. Size: height 4 mm to 6 mm, width 4 mm to 6 mm. Color: Green Group 144B.

*Sepals.*—Quantity: Five. Shape: Narrowly ovate with acute tip. Upper and lower texture: Leathery. Margin: Foliaceous appendages on three of the five sepals. Appearance: Dull. Color: Outer surface: Between Green Group 141B-C. Inner surface: Between Green Group 139B-C. Size: Length 20 mm to 25 mm, width 3 mm to 5 mm.

*Buds.*—Size: Height 10 mm to 15 mm, diameter 7 mm to 9 mm, Upon opening. Shape: Ovoid. Color: at ¼ opening, Green-White Group 157D.

*Flower.*—Duration: As a pot plant, flowers last from 10 to 15 days. Fragrance: Slightly spicy. Size: 30 mm to 40 mm in diameter. Depth: 15 mm to 20 mm. Form: Shape of flower when viewed from the side: Upon opening: Cupped to ovoid. Open flower: Flat. Color: Petals, upon opening: Upper surface: White Group 155A. Reverse surface: White Group 155A. Petals after opening: Upper surface: White Group 155A. Reverse surface: White Group 155A. General tonality: On open flower: Third day: White Group 155A. Afterwards: White Group 155A.

*Petals.*—Petal reflex: Outermost petals reflex backwards at opening. Fully open all petals reflex backwards. Texture: Smooth. Petal edge: Entire. Petal count: 35 to 40 on the average per flower. Petal size: Length 20 mm to 25 mm, width 15 mm to 20 mm. Shape: Outer petals: Round — ovate. Inner petals: Ovate. Apex: Rotundate. Base: Obtuse to rotundate.

*Petaloids.*—None.

*Reproductive organs.*—Stamen number: Approximately 65 to 70 on average per flower. Stamens length: 5 mm to 6 mm. Pollen: Color: Yellow-Orange Group 22A. Abundance: Heavy. Anthers: Size: 1 mm to 2 mm Color: Yellow-Orange Group 22A. Shape: Oblong. Filaments: Size: 3 mm to 5 mm. Color: Yellow Group 4A. Pistils number: Approximately 50 to 55 on average per flower. Stigmas: Location: Protrude more than the anthers. Color: Green-White Group 157A. Styles: Color: Green-White Group 157A.

Development:

*Vegetation.*—Dense.

*Blooming.*—Abundant.

*Aptitude to bear fruit.*—Poor.

*Resistance to diseases.*—Above average resistance to powdery mildew and Botrytis under normal growing conditions in Santa Barbara, Calif., USA. Hips/seeds has not been observed due to that the plant has never been grown to the stage of seed development, due to the fact, that the variety is developed for use as a flowering pot plant only.

*Winter hardiness & drought/heat tolerance.*—Due to the fact, that this variety is a potted flowering plant, developed indoor use only, the plant is not tested for winter hardiness or drought/heat tolerance.

The invention claimed is:

1. A new and distinct variety of Rose plant of the miniature class, substantially as herein illustrated and described as a distinct and novel rose variety due to its abundant white flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

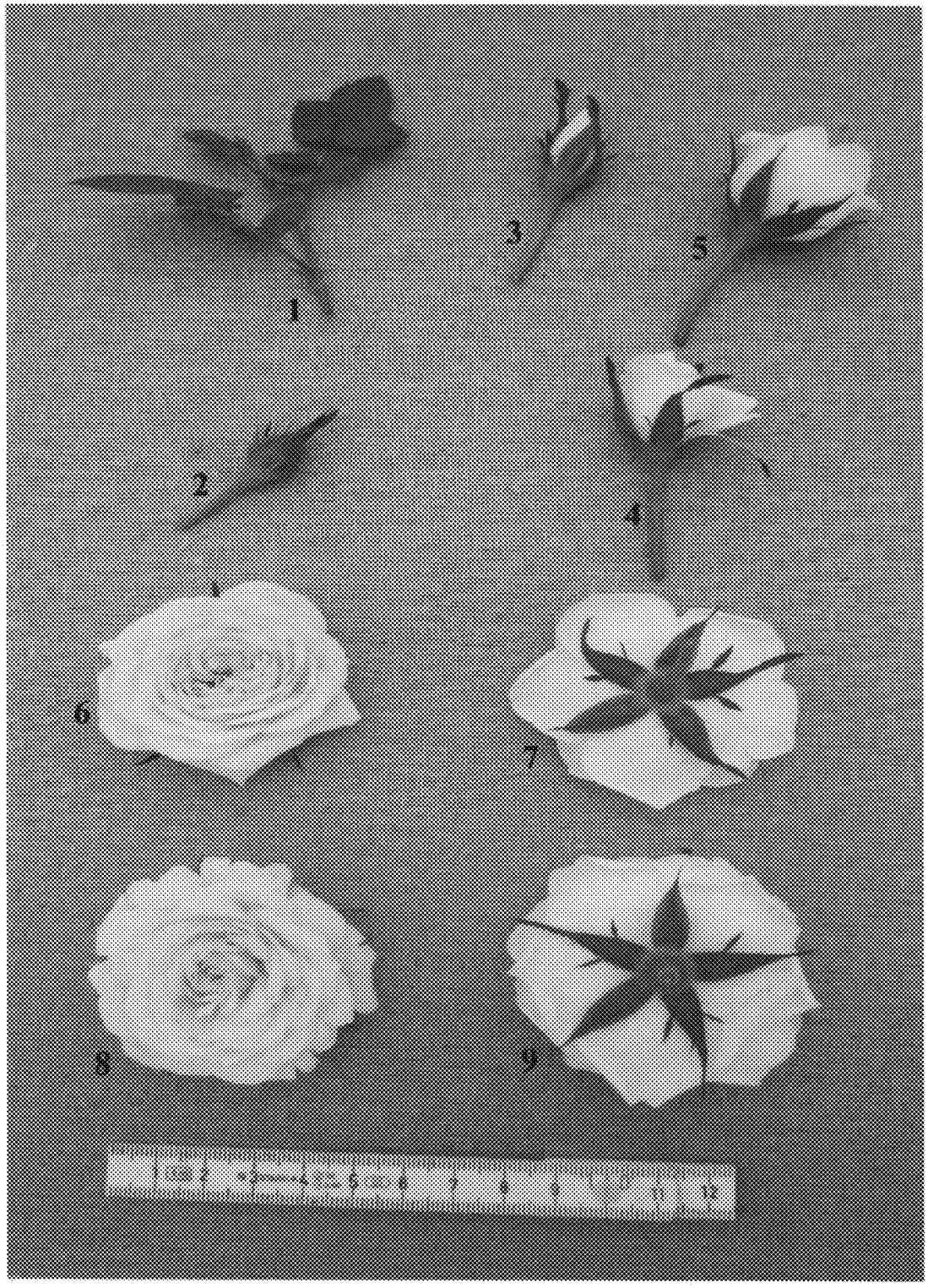
1
2
3
4
5
6
7
8
9

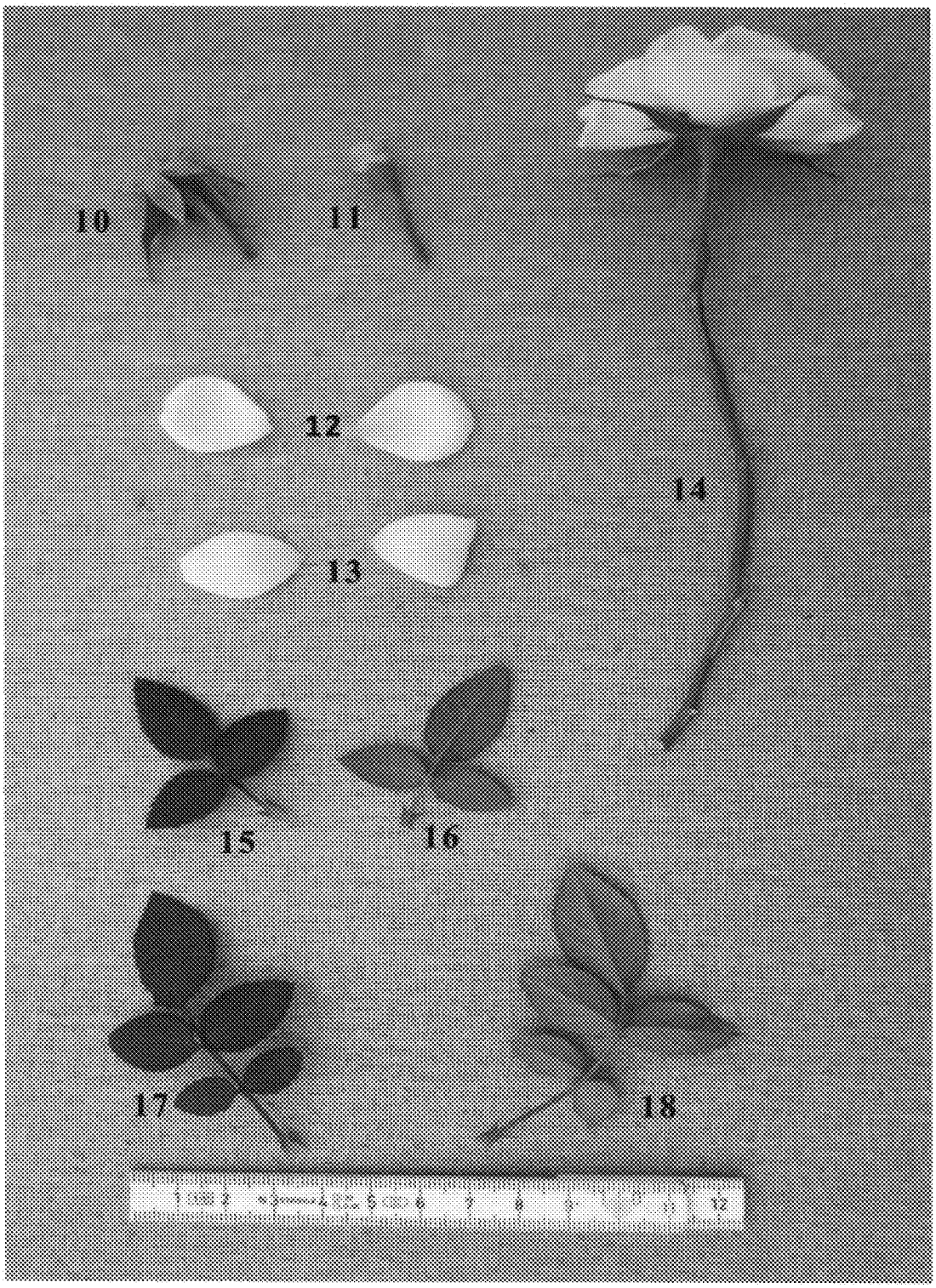
10
11
12
13
14
15
16
17
18